United States Patent
Lee

[11] Patent Number: 6,082,486
[45] Date of Patent: Jul. 4, 2000

[54] ARTICLE FOR COLLECTING SOUND FOR EARS

[76] Inventor: Young S. Lee, 500 S. Catalina, #310, Los Angeles, Calif. 90020

[21] Appl. No.: 09/243,339

[22] Filed: Feb. 1, 1999

[51] Int. Cl.⁷ .................................................... H04R 55/00
[52] U.S. Cl. ........................................... 181/136; 181/133
[58] Field of Search .................................. 181/129, 130, 181/133, 136

[56] References Cited

U.S. PATENT DOCUMENTS

| | | | |
|---|---|---|---|
| 4,724,922 | 2/1988 | Kalayjian . | |
| 4,768,613 | 9/1988 | Brown | 181/136 |
| 4,771,859 | 9/1988 | Breland | 181/136 |
| 4,997,056 | 3/1991 | Riley | 181/136 |
| 5,020,629 | 6/1991 | Edmundson et al. | 181/129 |
| 5,581,622 | 12/1996 | Sakurai . | |

Primary Examiner—Khanh Dang
Attorney, Agent, or Firm—John K. Park; Park & Sutton LLP

[57] ABSTRACT

The present invention is comprised of a headband 25 and one or more sound collectors (30, 75). The sound collectors (30, 75) collect sound waves and reflect toward the wearer's ears for louder reception. Some variations to the present invention can have one or more sound collectors (30, 75) that is parabolic in shape so the sound reflected off the collector surface is better focused toward the ear. Moreover, as an additional variation, one or more sound collectors (30, 75) can have one or more parabolic impressions (105) on the sound collector's inner surface (85) for better sound collection.

6 Claims, 7 Drawing Sheets

ARTICLE FOR COLLECTING SOUND FOR EARS

BACKGROUND

This present invention relates to an article that is designed to enhance a person's ability hear. It is a common understanding that a person's ear is used to collect the sound waves of various noise, and transmits onto the ear for the person to hear. However, many sounds are unheard by human ears because their loudness is insufficient for our ears to detect.

There have been several attempts to collect sound and amplify the loudness so the person can hear beyond the normal hearing. However, the most of these attempts has been with microphones, amplifiers, speakers, and headphones in order to capture, amplify, and deliver the sound audible to human ear. Although the quality of the sound thus electronically manipulated is good, the most of these sound amplifications require additional power source and additional equipment, some of them often heavy and bulky. Moreover, the effect of electronically generated electromagnetic field close to the person's ear is still being studied, and is known to have harmful effects in prolonged exposures.

Moreover, a person may prefer to hear better without electronic manipulations. This is especially true when the person wants to hear certain natural sounds, such as a bird chirpping or wave breaking against a rock.

For the foregoing reasons, there is a need for a new and improved article that will enhance the sound quality for human ear naturally without electronics.

SUMMARY

This present invention relates to an article for collecting sound for ears. This invention provides improve sound quality and loudness for human ears without electronically manipulating the sound quality.

The present invention is comprised of a headband and one or more sound collectors. One or more sound collectors is attached to the headband so that when the headband is worn by the user, one or more sound collectors would be near the person's ear or ears.

As some variations to the present invention, the article for collecting sound for ears can have one or more sound collectors that is parabolic in shape such that the sound reflected off the collector surface is focused toward the ear. Moreover, as an additional variation, one or more sound collectors can have one or more parabolic impressions on the collector surface so that the sound waves would be reflected off the parabolic impressions toward the ear.

The sound collector can be of various shapes and sizes as illustrated herebelow. Also different shaped and sized sound collectors can be detachably attached to the headband to adjust the sound quality according to the user's need and preference.

DESCRIPTIONS OF FIGURES

Figure 6:
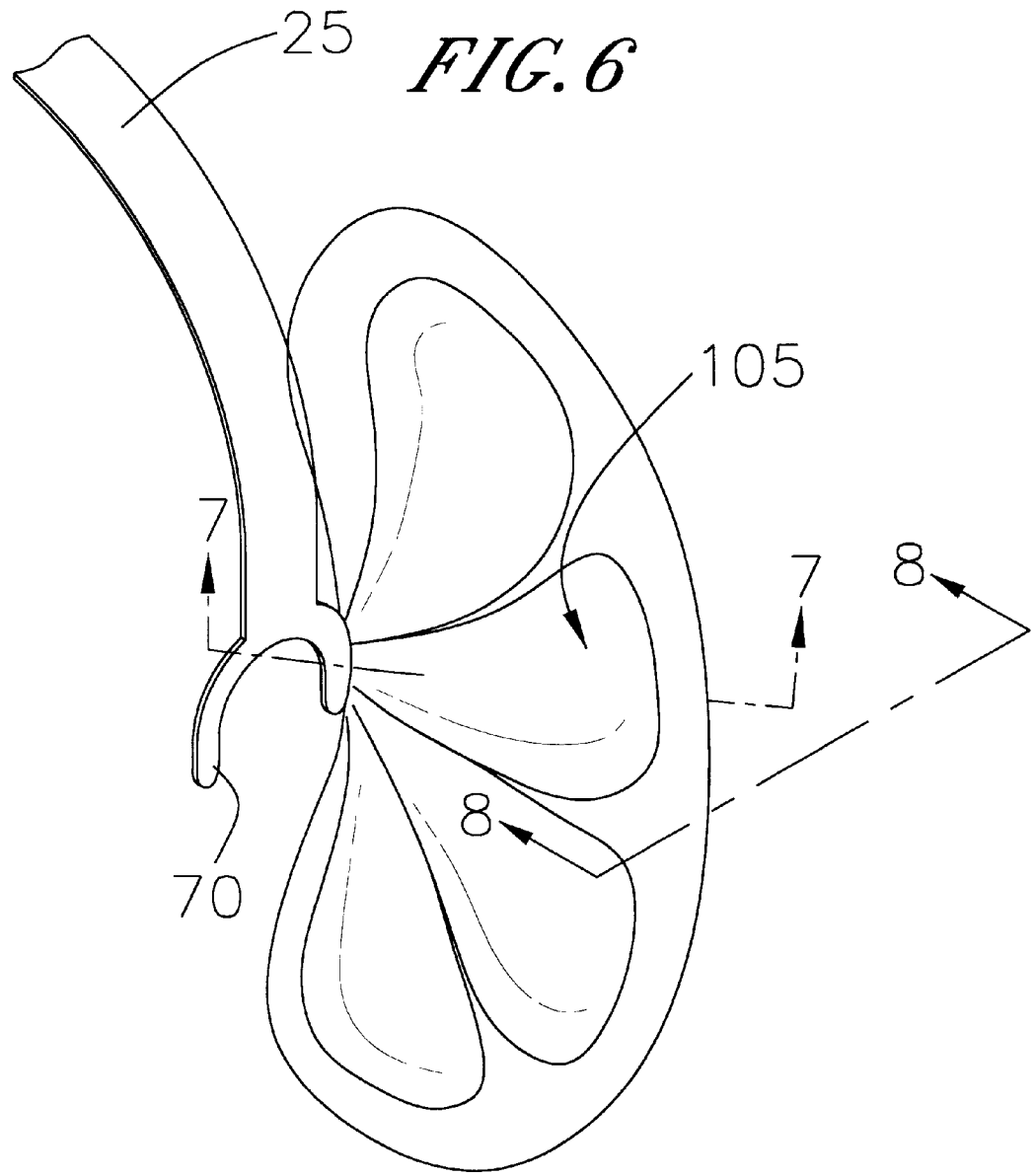

FIG. 6 another version of the present invention with a sound collector having more than one parabolic impressions.

Figure 7:
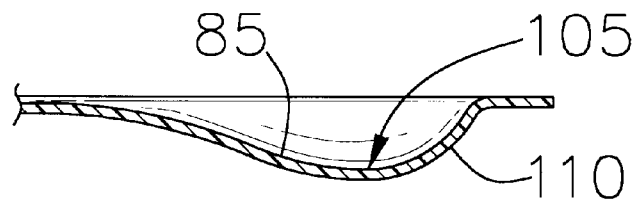

FIG. 7 is a cross-sectional view taken on line 7—7 of FIG. 6.

Figure 8:
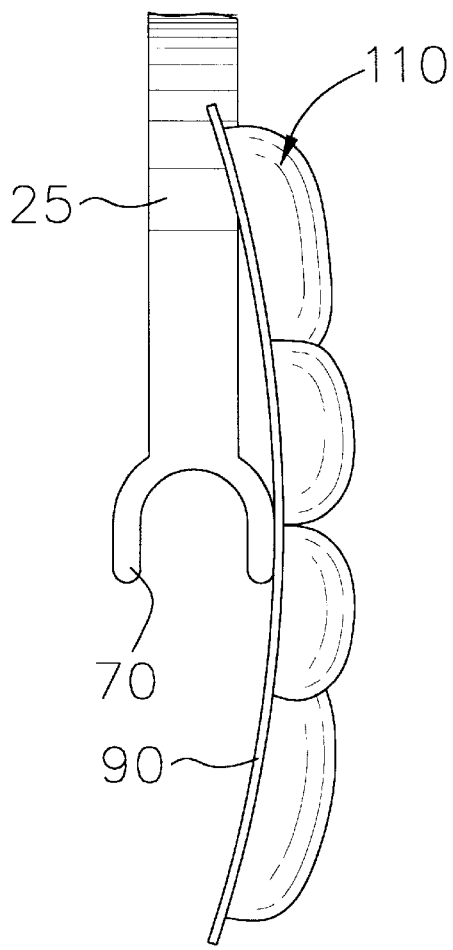

FIG. 8 is a side view of the present invention having a sound collector having more than one parabolic impressions.

Figure 9:
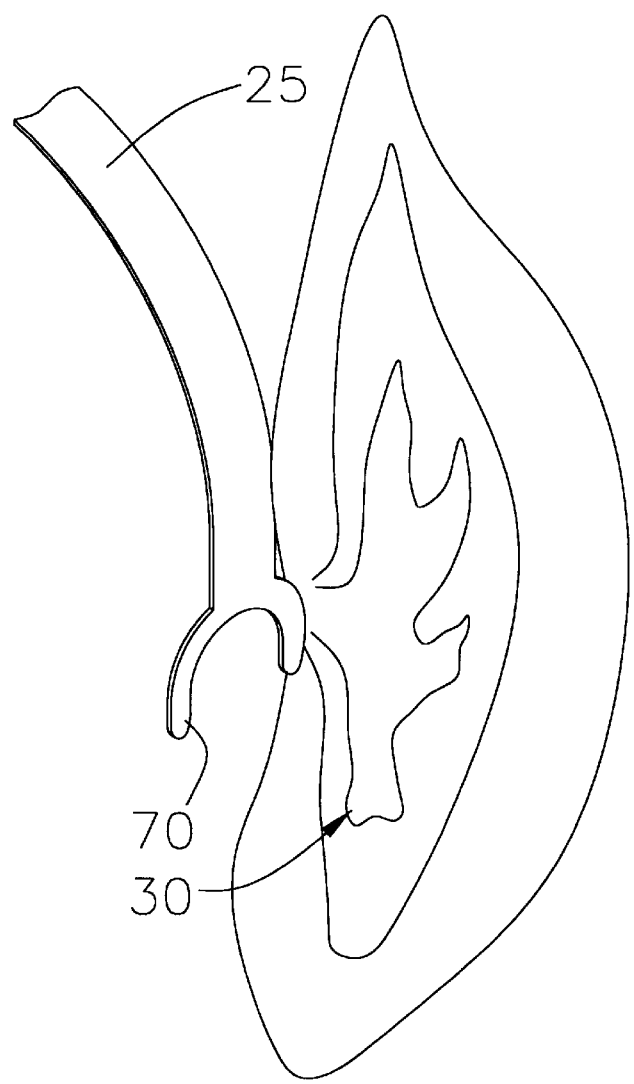

FIG. 9 another version of the present invention with a sound collector simulating an alien ear.

Figure 10:
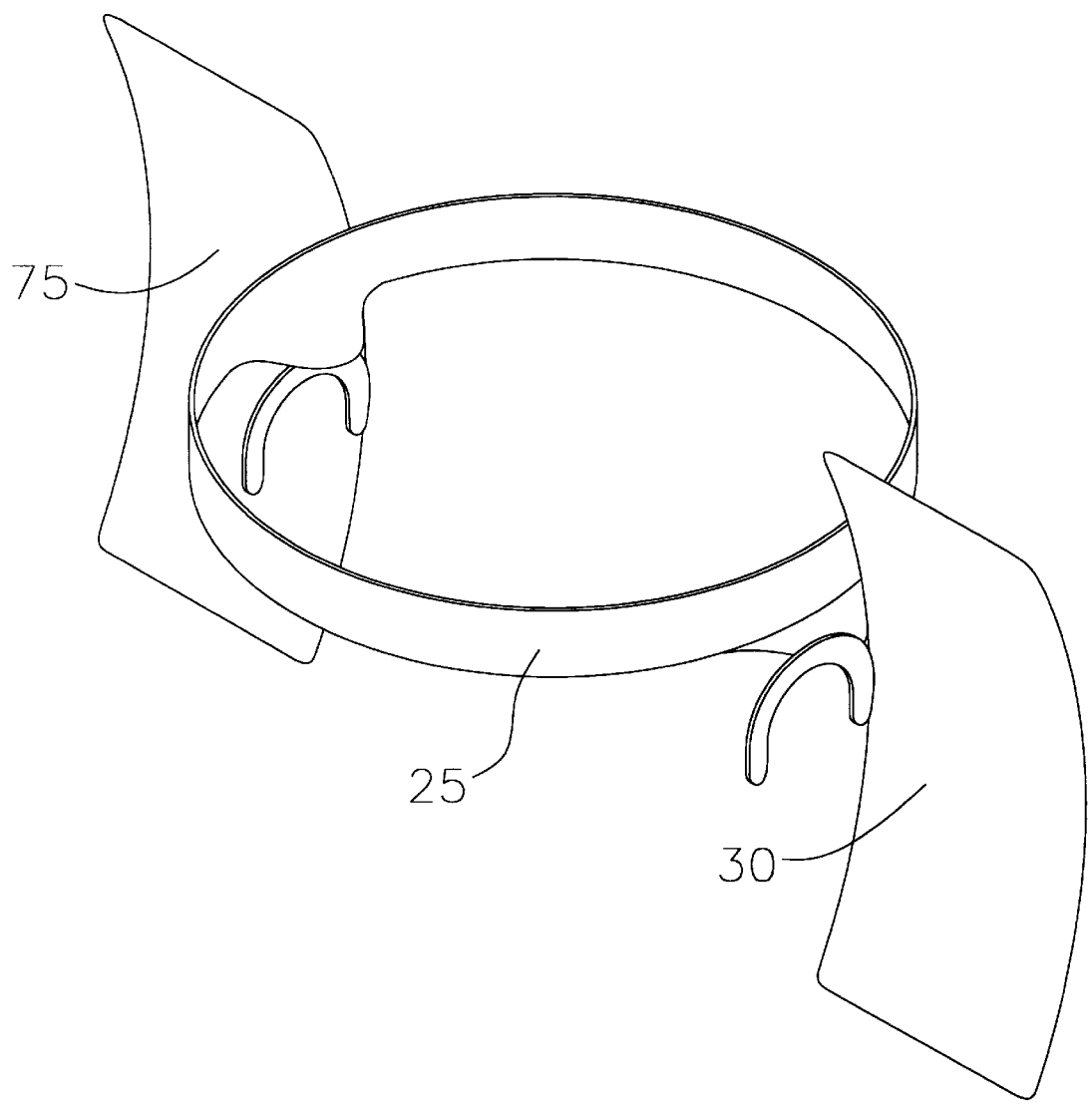

FIG. 10 another version of the present invention with a different headband.

DETAILED DESCRIPTION

This present invention relates to an article for collecting sound for ears 20. This invention provides improve sound quality and loudness for human ears without electronically manipulating the sound.

Figure 1:
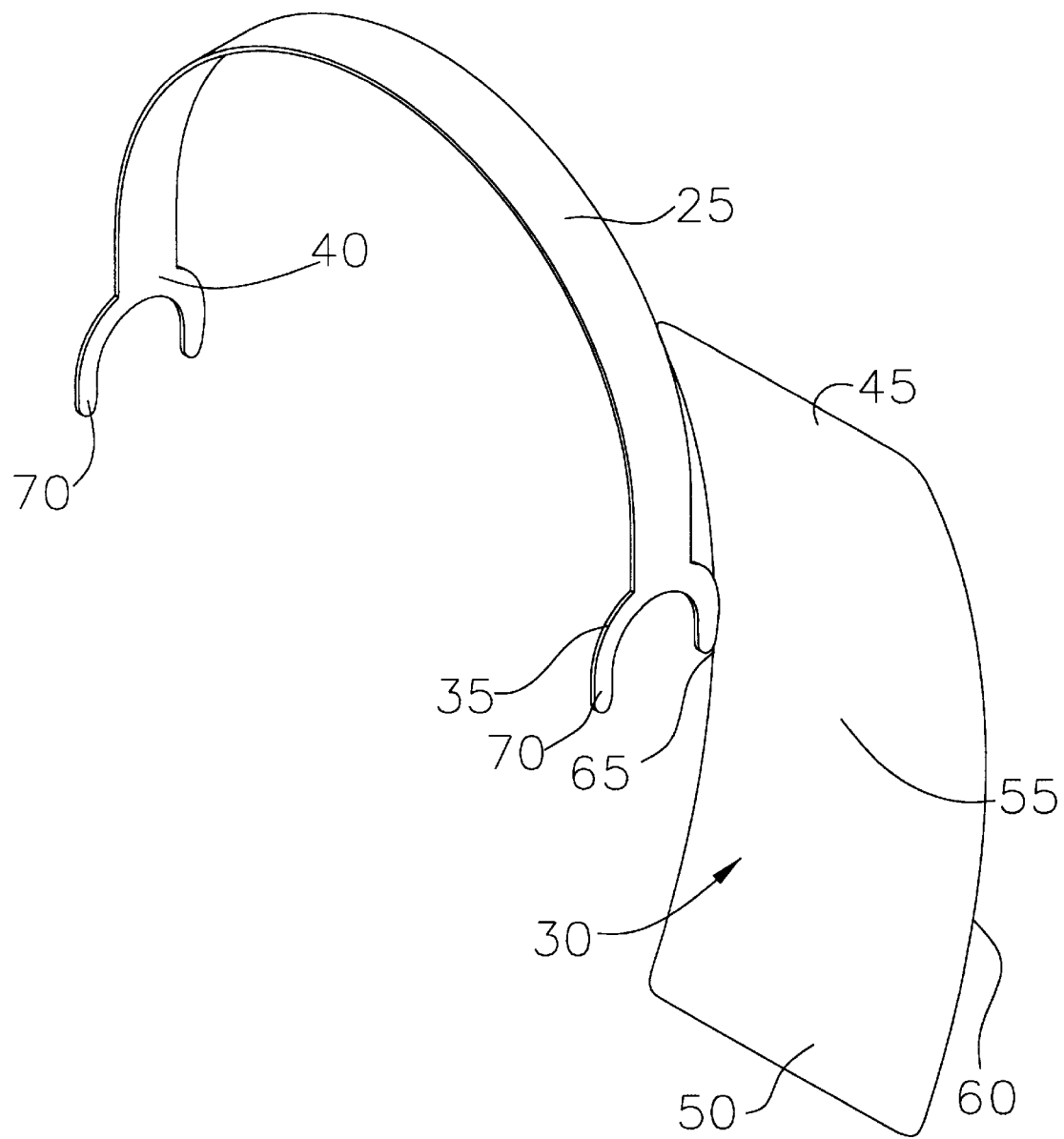
FIG. 1 is a perspective view of the present invention having one sound collector.

Referring to the drawings, FIG. 1 shows the present invention having a headband 25 and a first sound collector 30. The headband 25 has a first end 35 and a second end 40. Attached to the first end 35 of the headband 25 is the first sound collector 30 which has an upper end 45, a lower end 50, a middle portion 55, an edge 60, distanced from a user's ear and a base 65 approximating the user's ear. The headband 25, in this version, has a means to attach the headband 25 over the ears in a form of ear loops 70, while the headband 25 itself is designed to go over the wearer's head.

Figure 2:
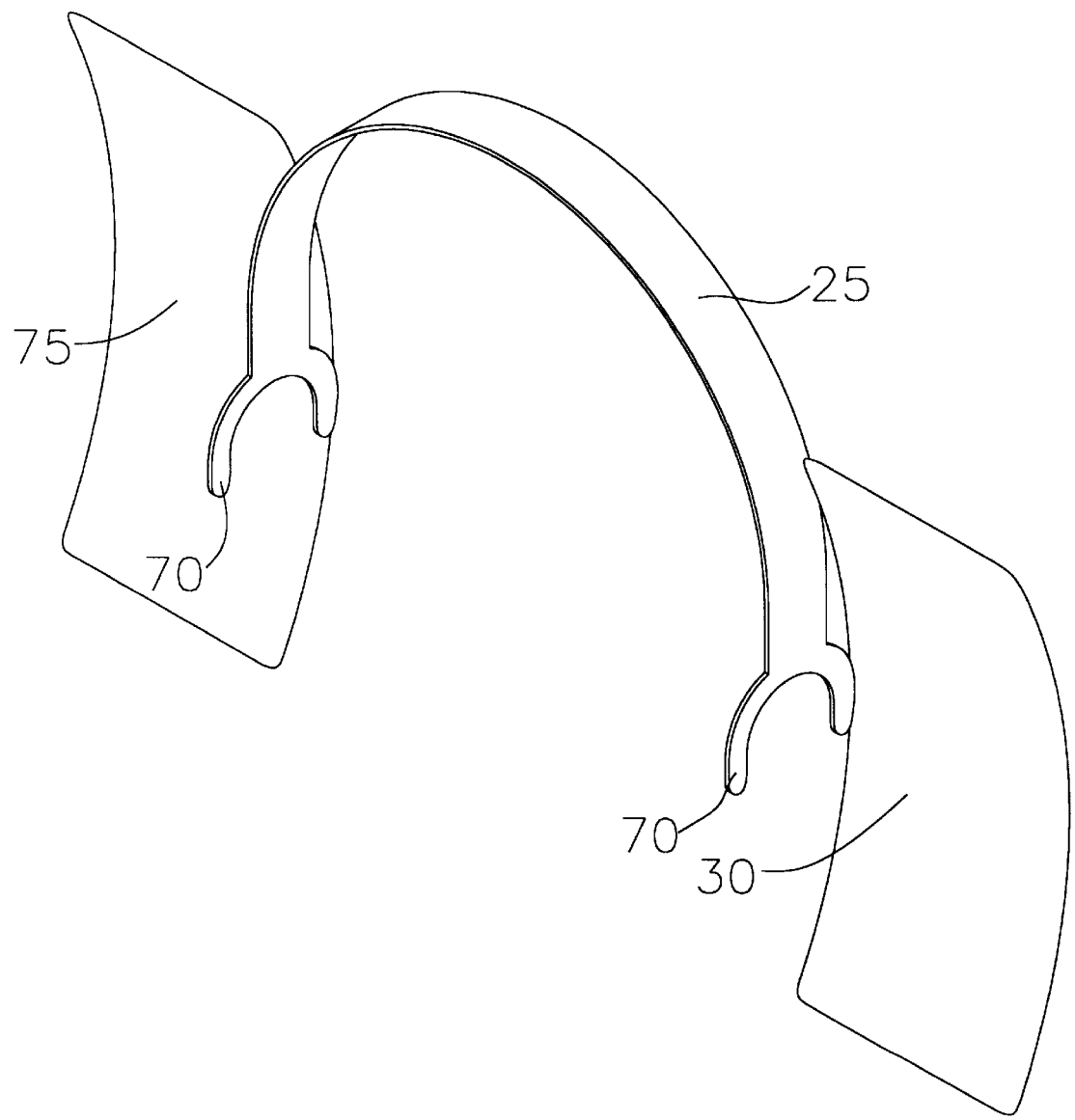
FIG. 2 is a perspective view of the present invention having two sound collectors.

FIG. 2 shows the present invention having the headband 25 and the first sound collector 30 and a second sound collector 75. The second sound collector 75 is attached to the second end 40 of the headband 24. The second sound collector 75 also has an upper end 45, a lower end 50, a middle portion 55, an edge 60, and a base 65. Although FIG. 2 illustrates a version of the present invention having the first sound collector 30 and the second sound collector 75 having about the same size and shape, the shape and size of the second sound collector 75 can have a different shape or size from the first sound collector 30.

Figure 3:
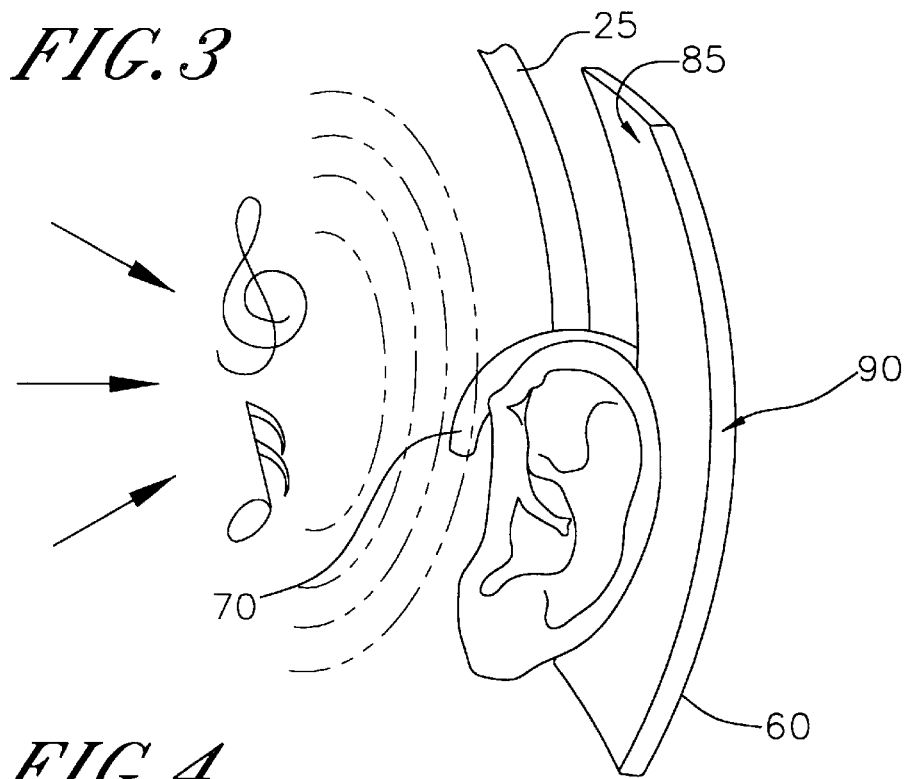
FIG. 3 is a side view of the present invention with a parabolic sound collector.
Figure 4:
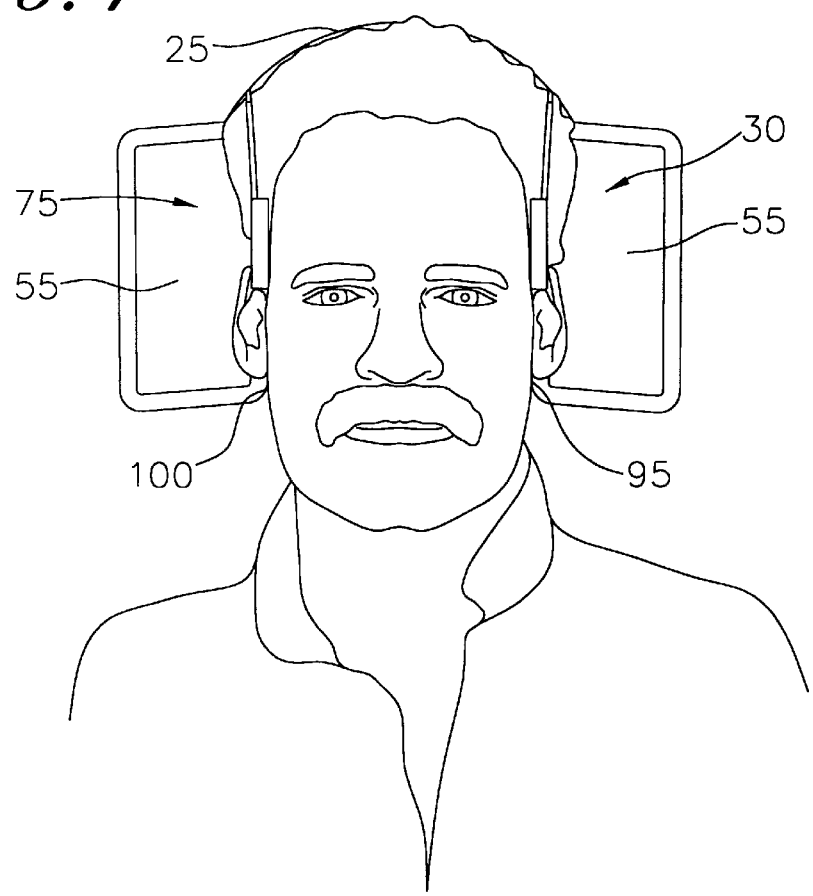
FIG. 4 is a front view of the present invention worn by a user.

FIG. 3 and FIG. 4 show the present invention having the first sound collector 30 wherein the first sound collector 30 is about parabolic in shape from the upper end 45 to the lower end 50 thereof so that at least one of the upper end 45 and the lower end 50 of the first sound collector 30 is situated closer to the front face 80 of the user than the middle portion 55 when the headband 25 is placed over the head. The FIG. 4 shows that both the first sound collector 30 and the second sound collector 75 having the parabolic shape from the upper end 45 to the lower end 50 of both the first sound collector 30 and the second sound collector 75 are set closer to the front face 80 than the middle portion 55 of each respective sound collectors 30, 75. The parabolic shape of the sound collectors 30, 75 allows the sound to reflect off an inner surface 85 of the sound collector 30, 75 and focus towards the middle portion 55 and towards the base 65 of the sound collector 30, 75.

FIG. 3 also shows a sound wall 90 at the edge 60 of the sound collector 30, 75. The sound wall 90 also reflects the sound waves toward the base 65 of the sound collector 30, 75.

As illustrated in FIG. 3 and FIG. 4, the sound collectors 30, 75 should be more than about two inches in height and more than about one inch in width, and the edge 60 of each sound collector 30, 75 should be at least about half the sound collector's width off respective side of the user's head 95, 100; a first side of the head 95, and a second side of the head 100. As the surface area of the inner surface 85 of the sound collector 30, 75 is directly proportional to the amount of sound reflected toward the base 65 of the sound collector 30, 75, it is preferable that the sound collector 30, 75 is more than about four inches in height and more than about three inches in width.

Figure 5:
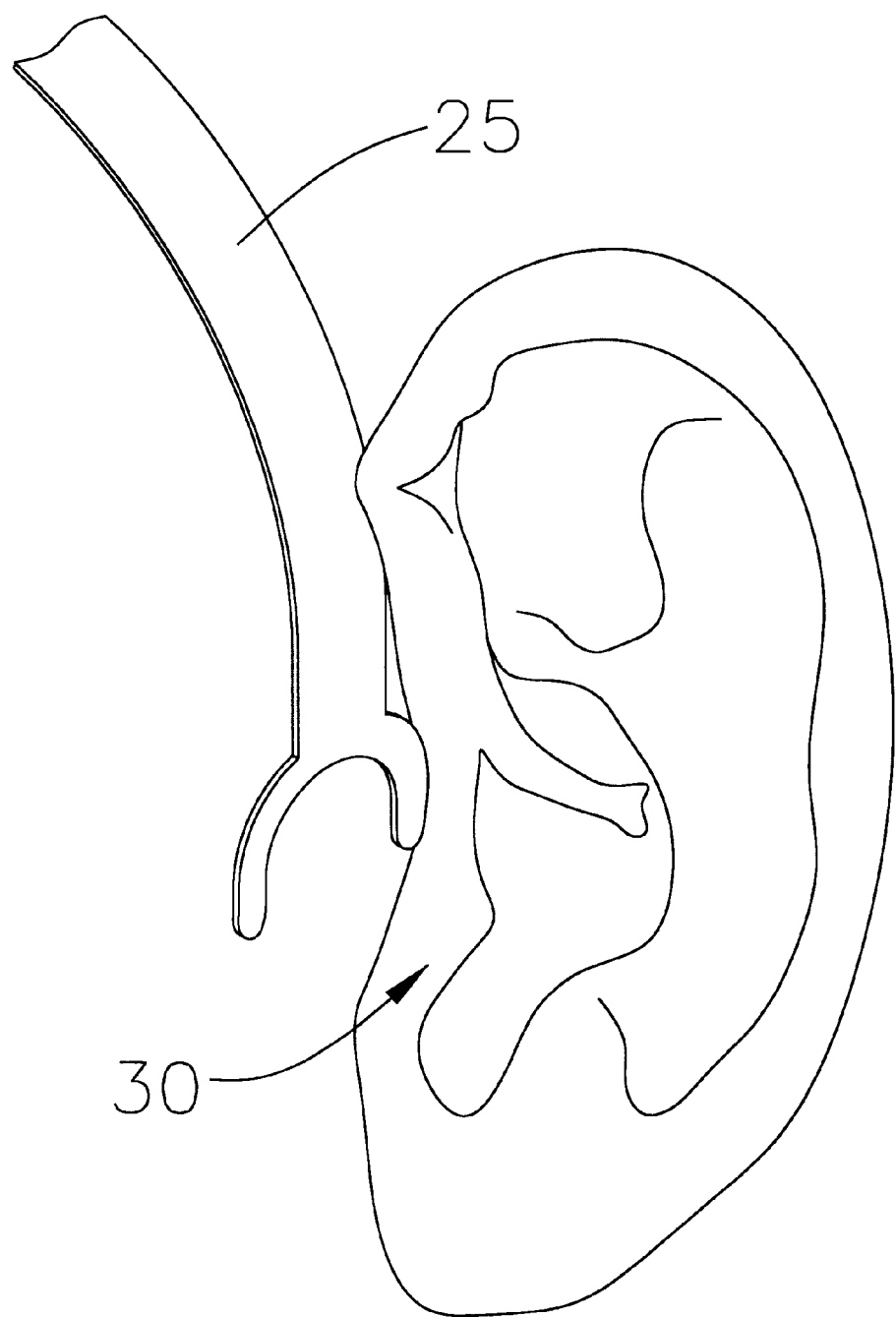
FIG. 5 is another version of the present invention with a sound collector simulating a human ear.

FIG. 5 illustrates the sound collector 30, 75 simulating a human ear. The sound collector 30, 75 is specially designed to simulate an auricle of a human ear, capitalizing on the intricate design of human ear; the sound collecting design that is believed to be the best suited for human. For the best performance, the size of the sound collectors 30, 75 should have the size of about three to four times an average human ear.

FIG. 6, FIG. 7, and FIG. 8 illustrate another version of the present invention with the sound collector 30, 75 having a plurality of parabolic impressions 105 into the inner surface 85 of the sound collector 30, 75. Each parabolic impression 105 is designed to reflect the sound waves toward the middle portion 55 and the base 65 of the sound collector 30, 75. FIG. 7 illustrates a cross-sectional view taken on line 7—7 of FIG. 6, and it demonstrates how the parabolic impressions 105 can be formed by having concave surface on the inner surface 85 and having convex surface on the outer surface 110 of the sound collector 30, 75.

FIG. 9 illustrates another version of the present invention with the sound collector 30, 75 simulating an alien ear, and FIG. 10 shows another version of the present invention with a different headband 25.

The material used for the sound collectors 30, 75 can be any material that can be formed into the desired shape. The sound collectors 30, 75 can be made out of plastic, leather, fabric, paper, metal, rubber, nylon, foam, and even malleable substances. Moreover, the inner surface 85 of the sound collector 30, 75 may be smooth, rough, hairy, fibrous, ribbed, and even porous. The inventor believes that the best result can be obtained by using a lightweight material that has a generally smooth surface.

The advantages of this invention are numerous. The user can hear sounds beyond the ability of an average human ear without using electronic means. The amount of sound collected can be adjusted by having different size sound collectors 30, 75 attached to the headband 25. The user can vary the quality of sound received between two ears by having different shaped and sized first sound collector 30 and the second sound collector 75. Furthermore, natural sounds are left natural without electronic modifications.

Although the invention has been described in considerable detail with reference to certain preferred versions thereof, other versions are possible. For example, a creative design may result in an embodiment that having telescoping, in height and/or width, sound collectors 30, 75.

What I claim is:

1. An article for collecting sound for ears comprising:
   a) a headband having a first end and a second end, designed to be placed over a head of a user; and
   b) a first sound collector having a lower end, an upper end, a middle portion, a base, and an edge, wherein the first sound collector is attached to the first end of the headband and, wherein the first sound collector further comprises of an inner surface and an outer surface, and the inner surface is formed with a plurality of parabolic impressions so that the sound waves would be reflected off the parabolic impressions toward the middle portion and toward the base.

2. An article for collecting sound for ears of claim 1, wherein the plurality of parabolic impressions are wider near the edge and are narrower toward the base.

3. The article of claim 1, wherein the first sound collector is parabolically curved from the upper end to the lower end thereof.

4. An article for collecting sound for ears comprising:
   a) a headband having a first end and a second end, designed to be placed over a head of a user;
   b) a first sound collector having a lower end, an upper end, a middle portion, a base, and an edge, wherein the first sound collector is attached to the first end of the headband and, wherein the first sound collector further comprises of an inner surface and an outer surface, and the inner surface is formed with a plurality of parabolic impressions so that the sound waves would be reflected off the parabolic impressions toward the middle portion and toward the base; and
   c) a second sound collector having a lower end, an upper end, a middle portion, a base, and an edge, wherein the second sound controller is attached to the second end of the headset, and wherein the second sound collector further comprises of an inner surface and an outer surface, and the inner surface is formed with the plurality of parabolic impressions so that the sound waves would be reflected off the parabolic impressions toward the middle portion and toward the base of the second sound collector.

5. The article of claim 4, wherein the first sound collector is parabolically curved from the upper end to the lower end thereof.

6. The article of claim 4, wherein the second sound collector is parabolically curved from the upper end to the lower end thereof.

* * * * *